United States Patent
Bouton et al.

(10) Patent No.: US 10,851,176 B2
(45) Date of Patent: Dec. 1, 2020

(54) METHODS OF ADMINISTERING NEUTRALIZING ANTI-PROTEASE NEXIN-1 ANTIBODIES TO TREAT HEMOPHILIA A

(71) Applicants: INSERM (INSTITUT NATIONAL DE LA SANTÉ ET DE LA RECHERCHE MÉDICALE), Paris (FR); UNIVERSITÉ PARIS DIDEROT—PARIS 7, Paris (FR); UNIVERSITÉ PARIS XIII PARIS-NORD, Villetaneuse (FR)

(72) Inventors: Marie-Christine Bouton, Paris (FR); Petrus Lenting, Le Kremlin-Bicêtre (FR); Cécile Denis, Le Kremlin-Bicêtre (FR); Olivier Christophe, Le Kremlin-Bicêtre (FR)

(73) Assignees: INSERM (INSTITUT NATIONAL DE LA SANTE ET DE LA RECHERCHE MEDICALE), Paris (FR); UNIVERSITE PARIS DIDEROT—PARIS 7, Paris (FR); UNIVERSITE PARIS XIII PARIS-NORD, Villetaneuse (FR)

( * ) Notice: Subject to any disclaimer, the term of this patent is extended or adjusted under 35 U.S.C. 154(b) by 275 days.

(21) Appl. No.: 15/565,933

(22) PCT Filed: Apr. 12, 2016

(86) PCT No.: PCT/EP2016/058034
§ 371 (c)(1),
(2) Date: Oct. 12, 2017

(87) PCT Pub. No.: WO2016/166110
PCT Pub. Date: Oct. 20, 2016

(65) Prior Publication Data
US 2018/0105603 A1    Apr. 19, 2018

(30) Foreign Application Priority Data

Apr. 13, 2015  (EP) .................................... 15305544

(51) Int. Cl.
*C07K 16/40* (2006.01)
*C07K 16/38* (2006.01)
*A61K 39/00* (2006.01)

(52) U.S. Cl.
CPC ............. *C07K 16/38* (2013.01); *C07K 16/40* (2013.01); *A61K 2039/505* (2013.01); *C07K 2317/76* (2013.01)

(58) Field of Classification Search
None
See application file for complete search history.

(56) References Cited

FOREIGN PATENT DOCUMENTS

WO    2012/110843 A1    8/2012
WO    WO-2012110843 A1 *  8/2012    ............. C07K 16/36

OTHER PUBLICATIONS

Edwards et al., J Mol Biol. Nov. 14, 2003;334(1):103-18.*
Lloyd et al., Protein Eng Des Sel. Mar. 2009;22(3):159-68. doi: 10.1093/protein/gzn058. Epub Oct. 29, 2008.*
Goel et al., J Immunol. Dec. 15, 2004;173(12):7358-67.*
Kanyavuz et al., Nat Rev Immunol. Jun. 2019;19(6):355-368. doi: 10.1038/S41577-019-0126-7.*
Janeway et al., Immunobiology, 3rd edition, 1997 Garland Publishing Inc., pp. 3:1-3:11.*
Rudikoff et al., Proc Natl Acad Sci USA. Mar. 1982;79(6):1979-83.*
Cannavo et al., Blood. Mar. 9, 2017;129(10):1245-1250. doi: 10.1182/blood-2016-06-720086. Epub Dec. 29, 2016.*
Product datasheet for GTX124069 downloaded Feb. 28, 2020 from https://www.genetex.com/PDF/Download?catno=GTX124069, 2 pages.*
Product datasheet for TA504602, downloaded Feb. 28, 2020 from https://cdn.origene.com/datasheet/ta504602.pdf, 2 pages.*
Wagner et al., Biochemistry. Mar. 22, 1988;27(6):2173-6. doi: 10.1021/bi00406a053.*
Boulaftali et al., Blood. Jan. 7, 2010;115(1):97-106. doi: 10.1182/blood-2009-04-217240. Epub Oct. 23, 2009.*
Boulaftali et al., Circulation. Mar. 29, 2011;123(12):1326-34. doi: 10.1161/CIRCULATIONAHA.110.000885. Epub Mar. 14, 2011.*
Bouton et al., "Emerging role of serpinE2/protease nexin-1 in hemostasis and vascular biology", Blood, Jan. 1, 2012, pp. 2452-2457, Web.
Boulaftali et al., "Platelet Protease Nexin-1, a Serpin That Strongly Influences Fibrinolysis and Thrombolysis", Circulation, Mar. 14, 2011, pp. 1326-1334, vol. 123, No. 12.
Al-Horani, R., "Serpin regulations of fibronolytic system: Implications for therapeutic applications in cardiovascular diseases", Cardiovascular and Hematological Agents in Medicinal Chemistry, Jan. 1, 2014, pp. 91-125, vol. 12, No. 2.

* cited by examiner

*Primary Examiner* — Michael Szperka
(74) *Attorney, Agent, or Firm* — W&C IP (57) ABSTRACT

The present invention relates to a method and compositions for the treatment of haemorrhagic diseases.

4 Claims, 3 Drawing Sheets

METHODS OF ADMINISTERING NEUTRALIZING ANTI-PROTEASE NEXIN-1 ANTIBODIES TO TREAT HEMOPHILIA A

FIELD OF THE INVENTION

The present invention relates to a method and compositions for the treatment of haemorrhagic diseases.

BACKGROUND OF THE INVENTION

Current treatments to control bleeding episodes in patients with haemophilia and more generally in patients with constitutive haemorrhagic diseases display many drawbacks. Prevention and treatment of bleeding disorders in haemophilia need the development of alternative therapeutic approaches that do not rely on FVIII or FIX replacement, because of the development of alloantibodies, called inhibitors, which abolish the activity of these coagulation factors. Treatment of these patients with an inhibitor is limited to FVIII- or IX-bypassing agents, such as recombinant FVIIa or plasma-derived activated prothrombin complex. However, these products are expensive and a substantial number of patients do not respond to these agents.

Accordingly, there is a need to develop an alternative therapeutic approaches and new drugs that will be suitable for preventing or treating haemorrhagic diseases and bleeding episodes in haemorrhagic diseases like haemophilia, preventing or treating rare bleeding diseases, constitutive haemorrhagic diseases and haemorrhagic diseases with deficiency in factor V, VIII, IX and/or XI. In this way, it has been suggested that characterization of new compounds for treatment of haemorrhagic diseases may be highly desirable.

The inventors propose an innovative approach consisting in targeting a natural negative regulator of thrombin, called protease nexin-1 or serpinE2, in the treatment of haemophilia. Although protease nexin-1 (PN-1) is the most powerful inhibitor of thrombin (Evans et al. 1991) and an effective inhibitor of FXIa (Knauer et al. 2000), such a concept has never been proposed up to now in the haemophilia context. The inventors showed that PN-1 is abundant in platelets but barely detectable in plasma. The inventors demonstrated that platelet PN-1 is a negative regulator of both thrombin activity and generation and that PN-1 deficiency facilitates coagulation in vivo (Boulaftali et al. 2010). Therefore, targeting PN-1 could thwart FVIII or IX deficiency.

Targeting the neutralization of PN-1, a natural anticoagulant is a radically new strategy for haemorrhagic disease treatment. There is no disclosure in the art of the role of protease nexin-1 in haemorrhagic diseases with deficiency in factor V, VIII, IX and/or XI, and the use of inhibitors of protease nexin-1 in the prevention or treatment of haemorrhagic diseases with deficiency in factor V, VIII, IX and/or XI.

SUMMARY OF THE INVENTION

The present invention relates to a protease nexin-1 (PN-1) expression or activity inhibitor for use in the prevention or treatment of haemorrhagic diseases in a subject in need thereof.

DETAILED DESCRIPTION OF THE INVENTION

The role of protease nexin-1 in haemorrhagic diseases was investigated by the inventors using human and mouse platelet-rich plasma (PRP) samples, mild, moderate and severe haemophilia A patients samples, mouse model of haemophilia, anti-PN-1 antibody and thrombin generation quantification.

The inventors aimed to investigate the capacity of neutralizing anti-PN-1 antibodies to correct thrombin generation in platelet-rich plasma (PRP) from hemophiliacs and from haemophilia A mice (FVIII-KO) and to investigate if neutralization of PN-1 should restore haemostasis in haemophilic condition. Adding a neutralizing anti-VIII antibody to the PRP of a control donor inhibits thrombin generation and mimics haemophilia, but under these experimental conditions, a neutralizing anti-PN-1 antibody restores thrombin generation to almost normal levels. These compelling results demonstrate that neutralizing PN-1 restore a sufficient level of thrombin generation in haemophiliacs to ensure haemostasis.

The inventors observed that anti-PN-1 antibody improves thrombin generation in hemophilic mice. The inventors also demonstrated that anti-PN-1 antibody improves thrombin generation in haemophilia patients. Furthermore, anti-PN-1 antibody improves thrombin generation in mild and moderate haemophilia patients but not in severe haemophilia patients. These findings establish a requirement for PN-1 inhibition as a specific anticoagulant in platelets and demonstrated that blocking PN-1 have a role in haemorrhagic disease treatment.

Therapeutic Methods and Uses

Accordingly, the present invention relates to a protease nexin-1 (PN-1) expression or activity inhibitor for use in the prevention or treatment of haemorrhagic diseases in a subject in need thereof.

As used herein, the term "subject" denotes a mammal. In a preferred embodiment of the invention, a subject according to the invention refers to any subject (preferably human) afflicted with or susceptible to be afflicted with haemorrhagic diseases. In another preferred embodiment, a subject according to the invention refers to any subject (preferably human) afflicted with or susceptible to be afflicted with haemorrhagic diseases with deficiency in factor V, VIII, IX and/or XI.

As used herein, the term "haemorrhagic diseases" has its general meaning in the art and refers to haemorrhagic diseases such as revised in the World Health Organisation Classification D65-D69. The term "haemorrhagic diseases" also refers to constitutive haemorrhagic diseases, Rare bleeding disorders, haemorrhagic diseases with deficiency in factor V, VIII, IX and/or XI. The term "haemorrhagic diseases" also refers to haemorrhagic diseases such as haemophilia, Hereditary factor VIII deficiency (Haemophilia NOS, Haemophilia A, classical Haemophilia); Hereditary factor IX deficiency (Christmas disease, Deficiency in factor IX with functional defect, Deficiency in plasma thromboplastin component [PTC], Haemophilia B); coagulation defects such as Von Willebrand disease, Angiohaemophilia, Factor VIII deficiency with vascular defect, Vascular haemophilia; Hereditary factor XI deficiency (Haemophilia C, Plasma thromboplastin antecedent [PTA] deficiency); Hereditary deficiency of other clotting factors (Congenital afibrinogenaemia, Deficiency in AC globulin, proaccelerin, Deficiency of factor I [fibrinogen], II [prothrombin], V [labile], VII [stable], X [Stuart-Prower], XII [Hageman], and XIII [fibrin-stabilizing], Dysfibrinogenaemia (congenital), Hypoproconvertinaemia, Owren disease); Haemorrhagic disorder due to circulating anticoagulants (Haemorrhage during long-term use of anticoagulants, Hyperheparinaemia, Increase in antithrombin, anti-VIIIa, anti-IXa, anti-Xa, and anti-Xia, Coding-Hint); Acquired coagulation factor deficiency (Deficiency of coagulation factor due to liver disease and vitamin K deficiency); Primary Thrombophilia (Activated protein C resistance [factor V Leiden mutation], Deficiency in antithrombin, protein C and protein S, Prothrombin gene mutation); Other Thrombophilia (Anticardiolipin syndrome, Antiphospholipid syndrome, Presence of the lupus anticoagulant); Purpura, Allergic purpura, Qualitative platelet defects, Thrombocytopenia, Capillary fragility (hereditary) and Vascular pseudohaemophilia. The term "haemorrhagic diseases" also refers to bleeding episodes in haemorrhagic diseases like haemophilia and other rare bleeding disorders.

In some embodiment, the haemorrhagic disease is a haemorrhagic disease with deficiency in factor V, VIII, IX and/or XI.

In some embodiment, the haemorrhagic disease is haemophilia.

In another embodiment, the inhibitor of the present invention is used in the prevention or treatment of bleeding episodes in haemorrhagic diseases.

As used herein, the term "protease nexin-1" or "PN-1" has its general meaning in the art and refers to the protease nexin-1 also known as SERPINE2. PN-1 has its general meaning in the art and refers to a member of serine protease inhibitors, termed serpins that are key regulators in many biologic events. PN-1 is a serpin that is barely detectable in plasma but found in many organs and produced by most cell types, including monocytes, platelets, and vascular cells. PN-1 is a 45- to 50-kDa glycoprotein that is encoded by the SERPINE2 gene on human chromosome 2q33-q35. PN-1 is a 378 amino acid residue single-chain containing 3 cysteine residues that do not form disulfide bonds within the protein core of the molecule (Bouton et al., 2012 and Mc Grogan et al 1988 Boulaftali et al., 2010).

The term "expression" when used in the context of expression of a gene or nucleic acid refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include messenger RNAs which are modified, by processes such as capping, polyadenylation, methylation, and editing, and proteins (e.g., phosphatidylserine receptor) modified by, for example, methylation, acetylation, phosphorylation, ubiquitination, SUMOylation, ADP-ribosylation, myristilation, and glycosylation.

An "expression inhibitor" refers to a natural or synthetic compound that has a biological effect to inhibit the expression of a gene.

A used herein the term "protease nexin-1 (PN-1) activity inhibitor" refers to any compound able to inhibit PN-1 activity and selectively blocks or inactivates PN-1. As used herein, the term "selectively blocks or inactivates" refers to a compound that preferentially binds to and blocks or inactivates PN-1 with a greater affinity and potency, respectively, than its interaction with the other sub-types or isoforms of the serpin family. Compounds that prefer PN-1, but that may also block or inactivate other serpin sub-types, as partial or full inhibitors, are contemplated. The "protease nexin-1 (PN-1) activity inhibitor" refers to compounds that block PN-1 interaction with proteins involved in coagulation such as thrombin and factor XIa (FXIa). The term "protease nexin-1 (PN-1) activity inhibitor" also relates to compounds that improve thrombin generation in the absence of factor V, VIII, IX and/or XI. Typically, an inhibitor of protease nexin-1 is an antibody, a peptide, a polypeptide, an aptamer or a small organic molecule.

Tests and assays for determining whether a compound is an inhibitor of protease nexin-1 are well known by the skilled person in the art such as described in Bouton et al., 2012 and Boulaftali et al., 2010.

In one embodiment, the PN-1 activity inhibitor of the invention is an aptamer. Aptamers are a class of molecule that represents an alternative to antibodies in term of molecular recognition. Aptamers are oligonucleotide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as E. coli Thioredoxin A that are selected from combinatorial libraries by two hybrid methods (Colas et al., 1996). Then after raising aptamers directed against PN-1 of the invention as above described, the skilled man in the art can easily select those inhibiting PN-1.

In another embodiment, the PN-1 activity inhibitor of the invention is an antibody (the term including "antibody portion").

In one embodiment of the antibodies or portions thereof described herein, the antibody is a monoclonal antibody. In one embodiment of the antibodies or portions thereof described herein, the antibody is a polyclonal antibody. In one embodiment of the antibodies or portions thereof described herein, the antibody is a humanized antibody. In one embodiment of the antibodies or portions thereof described herein, the antibody is a chimeric antibody. In one embodiment of the antibodies or portions thereof described herein, the portion of the antibody comprises a light chain of the antibody. In one embodiment of the antibodies or portions thereof described herein, the portion of the antibody comprises a heavy chain of the antibody. In one embodiment of the antibodies or portions thereof described herein, the portion of the antibody comprises a Fab portion of the antibody. In one embodiment of the antibodies or portions thereof described herein, the portion of the antibody comprises a F(ab')2 portion of the antibody. In one embodiment of the antibodies or portions thereof described herein, the portion of the antibody comprises a Fc portion of the antibody. In one embodiment of the antibodies or portions thereof described herein, the portion of the antibody comprises a Fv portion of the antibody. In one embodiment of the antibodies or portions thereof described herein, the portion of the antibody comprises a variable domain of the antibody. In one embodiment of the antibodies or portions thereof described herein, the portion of the antibody comprises one or more CDR domains of the antibody.

As used herein, "antibody" includes both naturally occurring and non-naturally occurring antibodies. Specifically, "antibody" includes polyclonal and monoclonal antibodies, and monovalent and divalent fragments thereof. Furthermore, "antibody" includes chimeric antibodies, wholly synthetic antibodies, single chain antibodies, and fragments thereof. The antibody may be a human or nonhuman antibody. A nonhuman antibody may be humanized by recombinant methods to reduce its immunogenicity in man.

Antibodies are prepared according to conventional methodology. Monoclonal antibodies may be generated using the method of Kohler and Milstein (Nature, 256:495, 1975). To prepare monoclonal antibodies useful in the invention, a mouse or other appropriate host animal is immunized at suitable intervals (e.g., twice-weekly, weekly, twice-monthly or monthly) with antigenic forms of PN-1. The animal may be administered a final "boost" of antigen within one week of sacrifice. It is often desirable to use an immunologic adjuvant during immunization. Suitable immunologic adjuvants include Freund's complete adjuvant, Freund's incomplete adjuvant, alum, Ribi adjuvant, Hunter's Titermax, saponin adjuvants such as QS21 or Quil A, or CpG-containing immunostimulatory oligonucleotides. Other suitable adjuvants are well-known in the field. The animals may be immunized by subcutaneous, intraperitoneal, intramuscular, intravenous, intranasal or other routes. A given animal may be immunized with multiple forms of the antigen by multiple routes.

Briefly, the antigen may be provided as synthetic peptides corresponding to antigenic regions of interest in PN-1. Following the immunization regimen, lymphocytes are isolated from the spleen, lymph node or other organ of the animal and fused with a suitable myeloma cell line using an agent such as polyethylene glycol to form a hydridoma. Following fusion, cells are placed in media permissive for growth of hybridomas but not the fusion partners using standard methods, as described (Coding, Monoclonal Antibodies: Principles and Practice: Production and Application of Monoclonal Antibodies in Cell Biology, Biochemistry and Immunology, 3rd edition, Academic Press, New York, 1996). Following culture of the hybridomas, cell supernatants are analyzed for the presence of antibodies of the desired specificity, i.e., that selectively bind the antigen. Suitable analytical techniques include ELISA, flow cytometry, immunoprecipitation, and western blotting. Other screening techniques are well-known in the field. Preferred techniques are those that confirm binding of antibodies to conformationally intact, natively folded antigen, such as non-denaturing ELISA, flow cytometry, and immunoprecipitation.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The Fc' and Fc regions, for example, are effectors of the complement cascade but are not involved in antigen binding. An antibody from which the pFc' region has been enzymatically cleaved, or which has been produced without the pFc' region, designated an F(ab')2 fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDRS). The CDRs, and in particular the CDRS regions, and more particularly the heavy chain CDRS, are largely responsible for antibody specificity.

It is now well-established in the art that the non CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody.

This invention provides in certain embodiments compositions and methods that include humanized forms of antibodies. As used herein, "humanized" describes antibodies wherein some, most or all of the amino acids outside the CDR regions are replaced with corresponding amino acids derived from human immunoglobulin molecules. Methods of humanization include, but are not limited to, those described in U.S. Pat. Nos. 4,816,567, 5,225,539, 5,585,089, 5,693,761, 5,693,762 and 5,859,205, which are hereby incorporated by reference. The above U.S. Pat. Nos. 5,585,089 and 5,693,761, and WO 90/07861 also propose four possible criteria which may used in designing the humanized antibodies. The first proposal was that for an acceptor, use a framework from a particular human immunoglobulin that is unusually homologous to the donor immunoglobulin to be humanized, or use a consensus framework from many human antibodies. The second proposal was that if an amino acid in the framework of the human immunoglobulin is unusual and the donor amino acid at that position is typical for human sequences, then the donor amino acid rather than the acceptor may be selected. The third proposal was that in the positions immediately adjacent to the 3 CDRs in the humanized immunoglobulin chain, the donor amino acid rather than the acceptor amino acid may be selected. The fourth proposal was to use the donor amino acid reside at the framework positions at which the amino acid is predicted to have a side chain atom within 3A of the CDRs in a three dimensional model of the antibody and is predicted to be capable of interacting with the CDRs. The above methods are merely illustrative of some of the methods that one skilled in the art could employ to make humanized antibodies. One of ordinary skill in the art will be familiar with other methods for antibody humanization.

In one embodiment of the humanized forms of the antibodies, some, most or all of the amino acids outside the CDR regions have been replaced with amino acids from human immunoglobulin molecules but where some, most or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgG1, IgG2, IgG3, IgG4, IgA and IgM molecules. A "humanized" antibody retains a similar antigenic specificity as the original antibody. However, using certain methods of humanization, the affinity and/or specificity of binding of the antibody may be increased using methods of "directed evolution", as described by Wu et al., *J. Mol. Biol.* 294:151, 1999, the contents of which are incorporated herein by reference.

Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (KAMA) responses when administered to humans.

In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

Thus, as will be apparent to one of ordinary skill in the art, the present invention also provides for F(ab')2 Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')2 fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

The various antibody molecules and fragments may derive from any of the commonly known immunoglobulin classes, including but not limited to IgA, secretory IgA, IgE, IgG and IgM. IgG subclasses are also well known to those in the art and include but are not limited to human IgG1, IgG2, IgG3 and IgG4. In a preferred embodiment, the PN-1 activity inhibitor of the invention is a Human IgG4.

In another embodiment, the antibody according to the invention is a single domain antibody. The term "single domain antibody" (sdAb) or "VHH" refers to the single heavy chain variable domain of antibodies of the type that can be found in Camelid mammals which are naturally devoid of light chains. Such VHH are also called "Nanobody®". According to the invention, sdAb can particularly be llama sdAb. The term "VHH" refers to the single heavy chain having 3 complementarity determining regions (CDRs): CDR1, CDR2 and CDR3. The term "complementarity determining region" or "CDR" refers to the hypervariable amino acid sequences which define the binding affinity and specificity of the VHH.

The VHH according to the invention can readily be prepared by an ordinarily skilled artisan using routine experimentation. The VHH variants and modified form thereof may be produced under any known technique in the art such as in-vitro maturation.

VHHs or sdAbs are usually generated by PCR cloning of the V-domain repertoire from blood, lymph node, or spleen cDNA obtained from immunized animals into a phage display vector, such as pHEN2. Antigen-specific VHHs are commonly selected by panning phage libraries on immobilized antigen, e.g., antigen coated onto the plastic surface of a test tube, biotinylated antigens immobilized on streptavidin beads, or membrane proteins expressed on the surface of cells. However, such VHHs often show lower affinities for their antigen than VHHs derived from animals that have received several immunizations. The high affinity of VHHs from immune libraries is attributed to the natural selection of variant VHHs during clonal expansion of B-cells in the lymphoid organs of immunized animals. The affinity of VHHs from non-immune libraries can often be improved by mimicking this strategy in vitro, i.e., by site directed mutagenesis of the CDR regions and further rounds of panning on immobilized antigen under conditions of increased stringency (higher temperature, high or low salt concentration, high or low pH, and low antigen concentrations). VHHs derived from camelid are readily expressed in and purified from the *E. coli* periplasm at much higher levels than the corresponding domains of conventional antibodies. VHHs generally display high solubility and stability and can also be readily produced in yeast, plant, and mammalian cells. For example, the "Hamers patents" describe methods and techniques for generating VHH against any desired target (see for example U.S. Pat. Nos. 5,800,988; 5,874,541 and 6,015,695). The "Hamers patents" more particularly describe production of VHHs in bacterial hosts such as *E. coli* (see for example U.S. Pat. No. 6,765,087) and in lower eukaryotic hosts such as moulds (for example Aspergillus or Trichoderma) or in yeast (for example Saccharomyces, Kluyveromyces, Hansenula or Pichia) (see for example U.S. Pat. No. 6,838,254).

In one embodiment, the inhibitor of the invention is a PN-1 expression inhibitor. PN-1 expression inhibitor for use in the present invention may be based on antisense oligonucleotide constructs. Anti-sense oligonucleotides, including anti-sense RNA molecules and anti-sense DNA molecules, would act to directly block the translation of PN-1 mRNA by binding thereto and thus preventing protein translation or increasing mRNA degradation, thus decreasing the level of PN-1 proteins, and thus activity, in a cell. For example, antisense oligonucleotides of at least about 15 bases and complementary to unique regions of the mRNA transcript sequence encoding PN-1 can be synthesized, e.g., by conventional phosphodiester techniques and administered by e.g., intravenous injection or infusion. Methods for using antisense techniques for specifically alleviating gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as PN-1 expression inhibitor for use in the present invention. PN-1 gene expression can be reduced by contacting the subject or cell with a small double stranded RNA (dsRNA), or a vector or construct causing the production of a small double stranded RNA, such that PN-1 expression is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes can also function as PN-1 expression inhibitor for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of PN-1 mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as PN-1 expression inhibitor can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing PN-1. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma virus; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in KRIEGLER (A Laboratory Manual," W. H. Freeman C. O., New York, 1990) and in MURRY ("Methods in Molecular Biology," vol. 7, Humana Press, Inc., Chiffon, N.J., 1991).

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g., SANBROOK et al., "Molecular Cloning: A Laboratory Manual," Second Edition, Cold Spring Harbor Laboratory Press, 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intravenous, intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In a further aspect, the inhibitor of the invention is a fusion protein.

The term "fusion protein" refers to the inhibitor according to the invention that is fused directly or via a spacer to at least one heterologous polypeptide.

According to the invention, the fusion protein comprises the inhibitor according to the invention that is fused either directly or via a spacer at its C-terminal end to the N-terminal end of the heterologous polypeptide, or at its N-terminal end to the C-terminal end of the heterologous polypeptide.

As used herein, the term "directly" means that the (first or last) amino acid at the terminal end (N or C-terminal end) of the inhibitor is fused to the (first or last) amino acid at the terminal end (N or C-terminal end) of the heterologous polypeptide.

In other words, in this embodiment, the last amino acid of the C-terminal end of said inhibitor is directly linked by a covalent bond to the first amino acid of the N-terminal end of said heterologous polypeptide, or the first amino acid of the N-terminal end of said inhibitor is directly linked by a covalent bond to the last amino acid of the C-terminal end of said heterologous polypeptide.

As used herein, the term "spacer" refers to a sequence of at least one amino acid that links the inhibitor of the invention to the heterologous polypeptide. Such a spacer may be useful to prevent steric hindrances.

In some embodiments, the heterologous polypeptide is a platelet targeting agent.

The term "platelet targeting agent" has its general meaning in the art and refers but not limited to agent targeting platelet that includes but not limited to von Willebrand factor (VWF), agents targeting specific platelet receptors glycoproteins (GP) such as GPIb-IX-V (or GPVI) and αIIbβ3 integrin, and agents described for example in U.S. Pat. No. 6,284,871 and US 2006/0160994.

In some embodiments, the heterologous polypeptide is a cell-penetrating peptide, a Transactivator of Transcription (TAT) cell penetrating sequence, a cell permeable peptide or a membranous penetrating sequence.

The term "cell-penetrating peptides" are well known in the art and refers to cell permeable sequence or membranous penetrating sequence such as penetratin, TAT mitochondrial penetrating sequence and compounds described in Bechara and Sagan, 2013; Jones and Sayers, 2012; Khafagy el and Morishita, 2012; Malhi and Murthy, 2012.

The fusion proteins of the invention may be produced by any technique known per se in the art, such as, without limitation, any chemical, biological, genetic or enzymatic technique, either alone or in combination.

Knowing the amino acid sequence of the desired sequence, one skilled in the art can readily produce said fusion proteins, by standard techniques for production of amino acid sequences. For instance, they can be synthesized using well-known solid phase method, preferably using a commercially available peptide synthesis apparatus (such as that made by Applied Biosystems, Foster City, Calif.) and following the manufacturer's instructions.

Alternatively, the fusion proteins of the invention can be synthesized by recombinant DNA techniques as is now well-known in the art. For example, these fragments can be obtained as DNA expression products after incorporation of DNA sequences encoding the desired (poly)peptide into expression vectors and introduction of such vectors into suitable eukaryotic or prokaryotic hosts that will express the desired fusion protein, from which they can be later isolated using well-known techniques.

Fusion proteins of the invention can be used in an isolated (e.g., purified) form or contained in a vector, such as a membrane or lipid vesicle (e.g. a liposome).

In specific embodiments, it is contemplated that fusion proteins according to the invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution.

The inventors demonstrated that PN-1 inhibitors improve thrombin generation in the absence of factor VIII. The inhibitor according to the invention presents an anti-haemorrhagic effect that does not rely on FVIII or FIX. Accordingly, the inhibitor according to the invention permits the use of low doses of coagulation factor or the diminution of their administration frequency and then avoids the development of coagulation factor resistance and the progression of the mild or moderate haemorrhagic diseases to severe haemorrhagic diseases.

Accordingly, the present invention also relates to the inhibitor according to the invention for use in the prevention of the progression of the mild or moderate haemorrhagic diseases to severe haemorrhagic diseases.

In some embodiment, the haemorrhagic disease is haemophilia A or haemophilia B.

The term "mild haemophilia A" has its general meaning in the art and refers to haemorrhagic disease defined by plasma FVIII of 5-40%.

The term "moderate haemophilia A" has its general meaning in the art and refers to haemorrhagic disease defined by plasma FVIII of 1-5%.

The term "severe haemophilia A" has its general meaning in the art and refers to haemorrhagic disease defined by plasma FVIII less than 1%.

The term "mild haemophilia B" has its general meaning in the art and refers to haemorrhagic disease defined by plasma FIX of 5-40%.

The term "moderate haemophilia B" has its general meaning in the art and refers to haemorrhagic disease defined by plasma FIX of 1-5%.

The term "severe haemophilia B" has its general meaning in the art and refers to haemorrhagic disease defined by plasma FIX less than 1%.

Accordingly, the present invention also relates to the inhibitor according to the invention for use in the prevention of the development of coagulation factor resistance.

In a further aspect, the present invention relates to the inhibitor according to the invention in combination with one or more coagulation factor for use in the prevention or treatment of haemorrhagic disease in a subject in need thereof.

The term "coagulation factor" has its general meaning in the art and refers to factor VIII (FVIII), factor IX (FIX), factor VIIa (FVIIa), plasma-derived activated prothrombin complex and fibrinogen. The term "coagulation factor" also relates to recombinant or purified coagulation factor.

Typically the inhibitor according to the invention and the haemorrhagic disease treatment as described above are administered to the subject in a therapeutically effective amount.

By a "therapeutically effective amount" of the inhibitor of the present invention as above described is meant a sufficient amount of the inhibitor. It will be understood, however, that the total daily usage of the inhibitors and compositions of the present invention will be decided by the attending physician within the scope of sound medical judgment. The specific therapeutically effective dose level for any particular subject will depend upon a variety of factors including the disorder being treated and the severity of the disorder; activity of the specific inhibitor employed; the specific composition employed, the age, body weight, general health, sex and diet of the subject; the time of administration, route of administration, and rate of excretion of the specific inhibitor employed; the duration of the treatment; drugs used in combination or coincidential with the specific inhibitor employed; and like factors well known in the medical arts. For example, it is well within the skill of the art to start doses of the inhibitor at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the inhibitor of the present invention for the symptomatic adjustment of the dosage to the subject to be treated. A medicament typically contains from about 0.01 mg to about 500 mg of the inhibitor of the present invention, preferably from 1 mg to about 100 mg of the inhibitor of the present invention. An effective amount of the drug is ordinarily supplied at a dosage level from 0.0002 mg/kg to about 20 mg/kg of body weight per day, especially from about 0.001 mg/kg to 7 mg/kg of body weight per day.

In a particular embodiment, the inhibitor according to the invention may be used in a concentration between 0.01 µM and 20 µM, particularly, the inhibitor of the invention may be used in a concentration of 0.01, 0.05, 0.1, 0.5, 1.0, 2.5, 5.0, 10.0, 15.0, 20.0 µM.

The therapeutically effective amount of the coagulation factor of the invention is well known in the art. Typically, the therapeutically effective amount of the coagulation factor relates to coagulation factor (such as FVIII) between about 10 IU to 300 IU/kg body weight, especially from about 10 IU to 100 IU/kg body weight. Particularly, the therapeutically effective amount of the coagulation factor relates to coagulation factor amount of 10.0, 15.0, 20.0, 25.0, 30.0, 35.0, 40.0 IU/kg body weight.

In a particular embodiment, the coagulation factor according to the invention may be used in low doses to avoid the development of coagulation factor resistance. Typically, the term "low doses" refers to coagulation factor (such as FVIII) between about 5 IU to 40 IU/kg body weight. Particularly, the term "low doses" refers to coagulation factor amount of about 5.0, 10.0, 15.0, 20.0, 25.0, 30.0, 35.0, 40.0 IU/kg body weight.

According to the present invention, the inhibitor of the invention is administered sequentially or concomitantly with one or more coagulation factor.

The present invention also relates to a method for preventing or treating haemorrhagic disease in a subject in need thereof, comprising the step of administering to said subject the PN-1 expression or activity inhibitor.

Pharmaceutical Composition and Kits of the Invention

The inhibitor of the invention may be used or prepared in a pharmaceutical composition.

In one embodiment, the invention relates to a pharmaceutical composition comprising the inhibitor of the invention and a pharmaceutical acceptable carrier for use in the prevention or treatment of haemorrhagic disease in a subject of need thereof.

Typically, the inhibitor of the invention may be combined with pharmaceutically acceptable excipients, and optionally sustained-release matrices, such as biodegradable polymers, to form therapeutic compositions.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising inhibitors of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The inhibitor of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

In addition to the inhibitors of the invention formulated for parenteral administration, such as intravenous or intramuscular injection, other pharmaceutically acceptable forms include, e.g. tablets or other solids for oral administration; liposomal formulations; time release capsules; and any other form currently used.

Pharmaceutical compositions of the invention may include any further agent which is used in the prevention or treatment of haemorrhagic disease.

In one embodiment, said additional active agents may be contained in the same composition or administrated separately.

In another embodiment, the pharmaceutical composition of the invention relates to combined preparation for simultaneous, separate or sequential use in the prevention and treatment of haemorrhagic disease.

The invention also provides kits comprising the PN-1 expression or activity inhibitor of the invention. Kits containing the PN-1 expression or activity inhibitor of the invention find use in therapeutic methods.

Screening Method

In a further aspect, the present invention relates to a method of screening a candidate compound for use as a drug for the prevention or treatment of haemorrhagic disease in a subject in need thereof, wherein the method comprises the steps of: i) providing candidate compounds and ii) selecting candidate compounds that blocks the action of protease nexin-1 (PN-1).

The present invention also relates to the candidate compound according to the invention for use in the prevention or treatment of haemorrhagic disease in a subject in need thereof.

In a further aspect, the present invention relates to a method of screening a candidate compound for use as a drug for the prevention or treatment of haemorrhagic disease in a subject in need thereof, wherein the method comprises the steps of:
    providing a cell, platelet-rich plasma (PRP), tissue sample or organism expressing the PN-1,
    providing a candidate compound such as small organic molecule, antibodies, peptide or polypeptide,
    measuring the activity of the PN-1,
    and selecting positively candidate compounds that blocks the action of PN-1 or inhibits PN-1 expression.

Methods for measuring the activity of the PN-1 are well known in the art. For example, measuring the PN-1 activity involves determining coagulation pathway activation on the PN-1 cloned and transfected in a stable manner into a CHO cell line or measuring thrombin generation in the presence or absence of the candidate compound (Bouton et al., 2012; Boulaftali et al., 2010).

Tests and assays for screening and determining whether a candidate compound is an inhibitor of PN-1 are well known in the art. In vitro and in vivo assays may be used to assess the potency and selectivity of the candidate compounds to reduce PN-1 activity.

Activities of the candidate compounds, their ability to bind PN-1 and their ability to inhibit PN-1 activity may be tested using isolated platelet-rich plasma (PRP) expressing PN-1, CHO cell line cloned and transfected in a stable manner by the human PN-1.

Cells expressing another serpin than PN-1 may be used to assess selectivity of the candidate compounds.

The invention will be further illustrated by the following figures and examples. However, these examples and figures should not be interpreted in any way as limiting the scope of the present invention.

Figure 1:
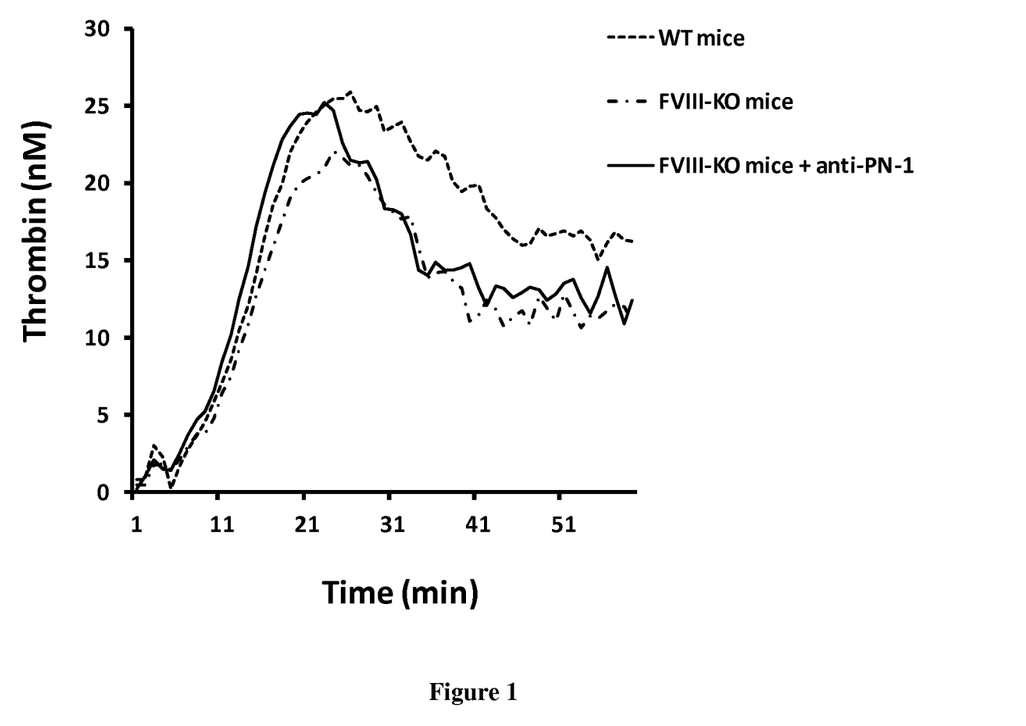
FIG. 1: Thrombin generation in haemophilic mice.

The thrombogram of FVIII-KO mice (-.-. curve) displays a prolonged time to peak and a reduced peak thrombin. The addition of the neutralizing anti-PN-1 antibody enhances thrombin generation in PRP from haemophilia mice (black curve). This is illustrated by the acceleration of thrombin generation (shorter time to peak) and the increase of the peak thrombin. These changes give rise to an increase thrombin generation velocity.

Figure 2:
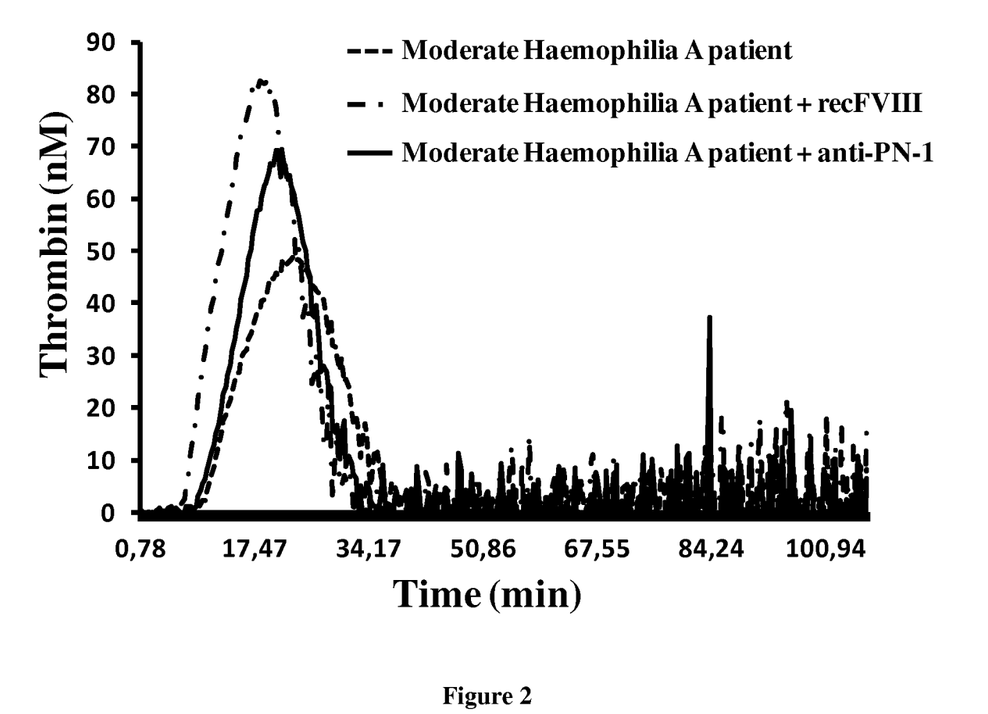
FIG. 2: Thrombin Generation in Haemophilica A Patient.
Figure 3:
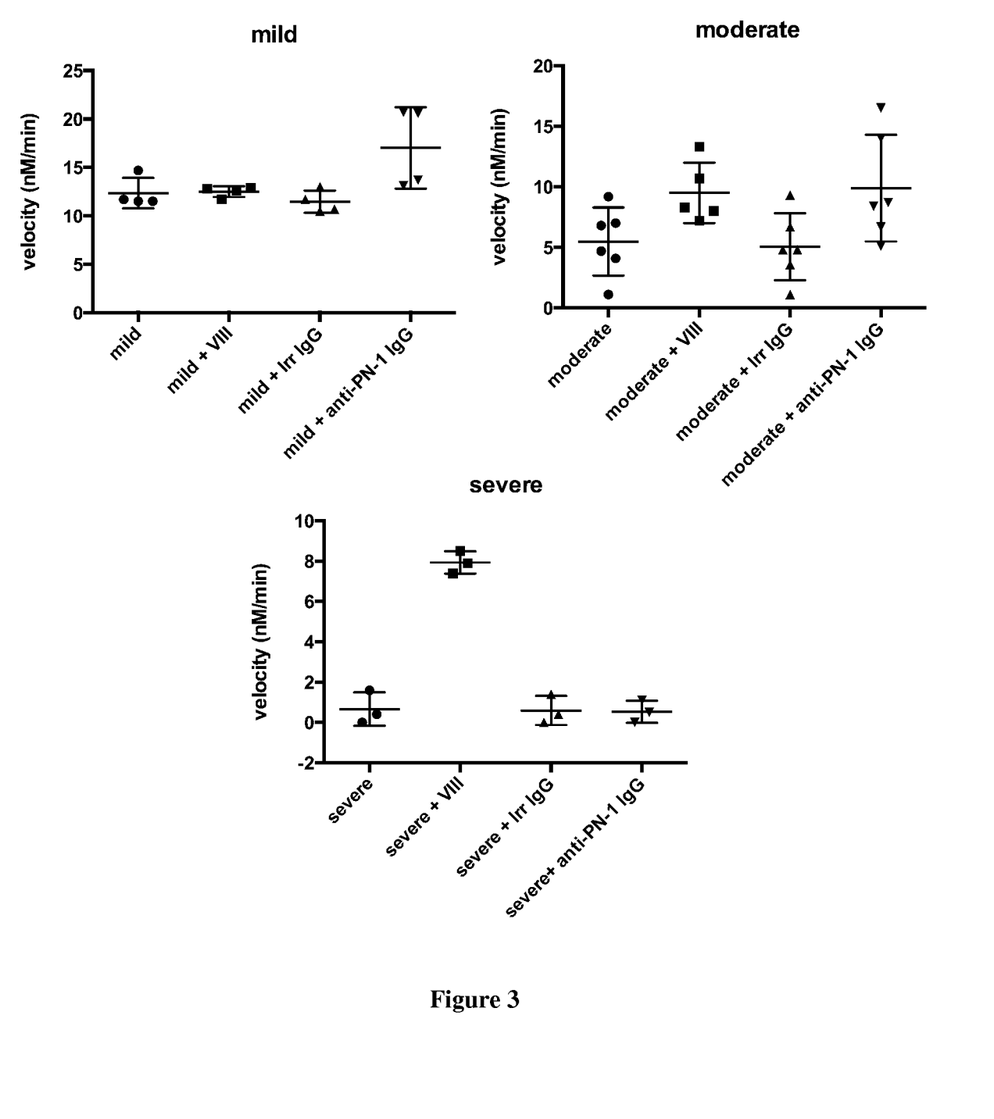
FIG. 3: Thrombin generation in mild, moderate and severe haemophilica A patient.

The thrombogram of patient with haemophilia (--- curve) displays prolonged lag time and time to peak and a reduced peak thrombin and a reduced endogenous thrombin potential. As observed with the addition of recombinant FVIII (-.-. curve), the neutralizing anti-PN-1 antibody enhances thrombin generation in PRP from patients with haemophilia A (black curve). This is illustrated by the acceleration of thrombin generation (shorter time to peak) and the increase of the peak thrombin. These changes give rise to an increase thrombin generation velocity.

velocity=Peak thrombin/(time to peak-lagtime)

As observed with recombinant FVIIII, the neutralizing anti-PN-1 antibody improves velocity of thrombin generation in patients with mild and moderate haemophilia. In contrast it has no effect in PRP from patients with severe haemophilia.

EXAMPLE

Material & Methods

The inventors determined thrombin generation in platelet-rich plasma (PRP) samples using the calibrated automated thrombogram (CAT) system containing the Fluoroskan Ascent fluorescence plate reader (Thrombinoscope BV, Maastricht, Netherlands). This is a method for quantifying continuous and dynamic properties of thrombin generation after addition of tissue factor in the sample. According to the manufacturer's instructions, thrombin generation is conducted, in triplicate, with 80 µl PRP in a total volume of 120 µl. Samples spiked with 20 µl thrombin calibrator (Diagnostica Stago, Asnieres, France) is run in parallel with each cycle of test sample.

PRP is incubated with the neutralizing anti-PN-1 polyclonal antibody for 20 min at 37° C., before being transferred to a pre-warmed (37° C.) microtiter plate with a mixture of TF and phospholipids. Twenty microliters of FluCaKit (fluorogenic substrate for thrombin) with CaC12 is then be automatically injected into all of the wells, starting the reaction. The fluorescence signal is read every 20 sec for 60 min in a fluoroskan Ascent reader (Thermo Labsystems) equipped with a 390/460 nm filter set, and thrombin generation curves is calculated using thrombinoscope software.

The thrombin generation assay (TGA) is a practical tool to determine global coagulation.

The parameters determined from a thrombin generation curve (thrombogram) are:
i) the endogenous thrombin potential (ETP), which corresponds to the area under the thrombin generation curve
ii) the peak thrombin, which corresponds to the maximal level of thrombin
iii) the lag time, which corresponds to the time taken to reach 2 nM thrombin
iv) the time to peak, which corresponds to the time taken to reach the peak height.

Thrombin Generation in Haemophilic Mice.

Citrated blood is drawn from the inferior vena cava from WT mice or FVIII-KO mice to prepare PRP (150 000 platelets/µl), which is preincubated or not with the anti-PN-1 antibody (150 µg/ml) for 30 min at RT. TGA is conducted in triplicate with 20 µl PRP plus 20 µl mixture reagent containing TF (0.5 pM) and phospholipids and 20 µl of fluorogenic substrate for thrombin with Cacl2 in a total volume of 60 µl.

Thrombin Generation in Haemophilica A Patient.

Samples from patients with severe (FVIII<1%), moderate (1%<FVIII<5%) and mild (5%<FVIII<40%) haemophilia are used. Citrated whole blood is drawn from patients to prepare PRP (150 000 platelets/µl), which is preincubated or not with the anti-PN-1 antibody (150 µg/ml), or recombinant FVIII (1 U/ml) for 30 min at RT. TGA is conducted in triplicate with 80 µl PRP plus 20 µl mixture reagent containing TF (0.5 pM) and phospholipids and 20 µl of fluorogenic substrate for thrombin with Cacl2 in a total volume of 120 µl.

Thrombin Generation in Mild, Moderate and Severe Haemophilica A Patient.

velocity=Peak thrombin/(time to peak-lagtime)

Velocity of thrombin generation was measured in PRP from patients with mild, moderate and severe haemophilia with recombinant FVIIII and the neutralizing anti-PN-1 antibody.

Results

PN-1 Inhibition in Mice

The thrombogram (thrombin generation) in haemophilic mice (FVIII-KO mice) (-.-. curve) displays a prolonged time to peak and a reduced peak thrombin. The addition of the neutralizing anti-PN-1 antibody enhances thrombin generation in PRP from haemophilia mice (black curve). This is illustrated by the acceleration of thrombin generation (shorter time to peak) and the increase of the peak thrombin. These changes give rise to an increase thrombin generation velocity (FIG. 1).

PN-1 Inhibition in Human

Thrombin Generation in Haemophilica A Patient.

As previously described, the classic thrombogram of patient with haemophilia (--- curve) displays prolonged lag time and time to peak and a reduced peak thrombin and a reduced endogenous thrombin potential. As observed with the addition of recombinant FVIII (-.-. curve), the neutralizing anti-PN-1 antibody can enhance thrombin generation in PRP from patients with haemophilia A. (- curve) This is illustrated by the acceleration of thrombin generation (shorter time to peak) and the increase of the peak thrombin. These changes give rise to an increase thrombin generation velocity (FIG. 2).

Thrombin Generation in Mild, Moderate and Severe Haemophilica A Patient.

Severe, Moderate and Mild phenotypes are defined by plasma FVIII of less than 1%, 1-5% and 5%-40%, respectively. Moderate and mild patients account for about 60% of the haemophilia A population.

As observed with recombinant FVIIII, the neutralizing anti-PN-1 antibody improves velocity (Peak thrombin/(time to peak-lagtime)) of thrombin generation in patients with mild and moderate haemophilia. In contrast it has no effect in PRP from patients with severe haemophilia (FIG. 3).

Anti-PN-1 antibody improves thrombin generation in mild and moderate haemophilia patients but not in severe haemophilia patients. These findings establish a requirement for PN-1 inhibition as a specific anticoagulant in platelets and demonstrated that blocking PN-1 have a role in haemorrhagic disease treatment.

REFERENCES

Throughout this application, various references describe the state of the art to which this invention pertains. The disclosures of these references are hereby incorporated by reference into the present disclosure.

Boulaftali Y, Adam F, Venisse L, Ollivier V, Richard B, Taieb S, Monard D, Favier R, Alessi M C, Bryckaert M, Arocas V, Jandrot-Perrus M, Bouton M C. Anticoagulant and antithrombotic properties of platelet protease nexin-1. *Blood.* 2010; 115: 97-106.

Bouton M C, Boulaftali Y, Richard B, Arocas V, Michel J B, Jandrot-Perrus M. Emerging role of serpinE2/protease nexin-1 in hemostasis and vascular biology. *Blood.* 2012 Mar. 15; 119(11):2452-7.

Evans D L, McGrogan M, Scott R W, Carrell R W. Protease specificity and heparin binding and activation of recombinant protease nexin I. *The Journal of biological chemistry.* 1991; 266: 22307-12.

Knauer D J, Majumdar D, Fong P C, Knauer M F. SERPIN regulation of factor XIa. The novel observation that protease nexin 1 in the presence of heparin is a more potent inhibitor of factor Xia than C1 inhibitor. *The Journal of biological chemistry.* 2000; 275: 37340-6.

McGrogan M, Kennedy J, Li M P, et al. Molecular cloning and expression of two forms of human protease nexin I. *Biotechnology.* 1988; 6:172-177.

The invention claimed is:

1. A method for treating mild or moderate haemophilia A in a subject in need thereof, comprising the step of administering to said subject a protease nexin-1 activity inhibitor, wherein the protease nexin-1 activity inhibitor is an anti-protease nexin-1 neutralizing antibody.

2. The method of claim 1, wherein the protease nexin-1 activity inhibitor is administered in combination with one or more coagulation factors.

3. The method of claim 2, wherein the one or more coagulation factors is selected from the group consisting of factor VIII, factor IX, factor Vila, plasma-derived activated prothrombin complex and fibrinogen.

4. The method of claim 1, wherein the protease nexin 1 activity inhibitor is fused to a platelet targeting agent.

* * * * *